United States Patent [19]

Sacks et al.

[11] Patent Number: 5,205,845
[45] Date of Patent: Apr. 27, 1993

[54] MECHANICAL GAS CHROMATOGRAPHY INJECTION VALVES AND COLUMN MULTIPLEXING TECHNIQUES

[75] Inventors: Richard D. Sacks, Ann Arbor; Anita J. Peters, Ypsilanti, both of Mich.

[73] Assignee: The Regents of the University of Michigan, Ann Arbor, Mich.

[21] Appl. No.: 817,306

[22] Filed: Jan. 6, 1992

Related U.S. Application Data

[63] Continuation-in-part of Ser. No. 590,174, Sep. 28, 1990, Pat. No. 5,096,471, and a continuation-in-part of Ser. No. 710,703, Jun. 5, 1991, Pat. No. 5,141,532, and a continuation-in-part of Ser. No. 717,356, Jun. 18, 1991, Pat. No. 5,141,534.

[51] Int. Cl.⁵ .................................................. B01D 15/08
[52] U.S. Cl. .................................... 55/197; 55/208; 55/386; 73/23.41
[58] Field of Search .............. 55/67, 197, 386, 208, 55/267–269; 73/23.41

[56] References Cited

U.S. PATENT DOCUMENTS

| | | | |
|---|---|---|---|
| 2,757,541 | 8/1956 | Watson et al. | 73/23.41 X |
| 2,972,246 | 2/1961 | Reinecke et al. | 73/23 |
| 2,981,092 | 4/1961 | Marks | 55/67 X |
| 3,000,218 | 9/1961 | Marks et al. | 55/67 X |
| 3,119,251 | 1/1964 | Bowers | 73/23 |
| 3,136,616 | 6/1964 | Thompson | 55/67 |
| 3,201,922 | 8/1965 | Villalobos | 55/67 |
| 3,201,971 | 8/1965 | Villalobos | 55/67 X |
| 3,223,123 | 12/1965 | Young | 55/67 X |
| 3,477,207 | 11/1969 | Auger | 55/197 |
| 3,630,371 | 12/1971 | Hrdina | 55/67 X |
| 3,676,649 | 7/1972 | Burk | 235/151.3 |
| 3,798,973 | 3/1974 | Estey | 73/23.1 X |
| 4,470,832 | 9/1984 | Sugawara et al. | 55/197 |
| 4,617,032 | 10/1986 | Wells | 55/67 |
| 4,932,272 | 6/1990 | Hogg | 73/864.83 |
| 5,096,471 | 3/1992 | Sacks et al. | 55/67 |

OTHER PUBLICATIONS

Analytical Chemistry, "Theoretical Aspects and Practical Potentials of Rapids Gas Analysis in Capillary Gas Chromatography", Apr. 1987, vol. 59, No. 7, pp. 1007–1015, R. Tijssen et al.

Primary Examiner—Robert Spitzer
Attorney, Agent, or Firm—Harness, Dickey & Pierce

[57] ABSTRACT

Several embodiments of gas chromatography systems are disclosed incorporating mechanical sample injection valves. The injection valves incorporate a delivery tube having an outlet which is swept past the inlet of a separation column to provide a short duration inlet plug into the separation column. Carrier gas and sample gas flow is managed through the valve to prevent inadvertent injection after an injection is desired and to assure that the sample is not contaminated by past sample flow. Embodiments of injections valve are described for providing inputs into several gas chromatography columns. In addition, a gas chromatography system is described in which multiple columns are used which are time multiplexed with a single detector to produce a complex combined chromatogram from the plural columns. By appropriate selection of column characteristics and injection sequence, the resulting chromatogram can provide an overlay of chromatograms which provide good resolution of all the constituents of the mixture of interest within a short analysis time.

31 Claims, 6 Drawing Sheets

MECHANICAL GAS CHROMATOGRAPHY INJECTION VALVES AND COLUMN MULTIPLEXING TECHNIQUES

CROSS-REFERENCE TO RELATED APPLICATIONS

This application is a continuation-in-part of the following co-pending patent applications: U.S. patent application Ser. No. 590,174, filed on Sept. 28, 1990, entitled "Gas Chromatography System and Method", now U.S. Pat. No. 5,096,471; U.S. patent application Ser. No. 710,703, filed on June 5, 1991, entitled "Thermal Modulation Inlet For Gas Chromatography System", now U.S. Pat. No. 5,141,532; and U.S. patent application Ser. No. 717,356, filed on June 18, 1991, entitled "Sample Collection And Inlet System For Gas Chromatography Apparatus", now U.S. Pat. No. 5,141,534.

BACKGROUND AND SUMMARY OF THE INVENTION

This invention relates to apparatuses and methods for conducting gas chromatography separation procedures, and particularly to mechanical inlet systems for such apparatuses, and approaches toward multiplexing multiple columns.

Gas chromatography is a widely employed technique for the separation and analysis of complex mixtures of volatile organic and inorganic compounds. The analyte mixture is separated into its components by eluding them from a column having a sorbent by means of moving gas.

Gas chromatography procedures can be classified into two major divisions: gas-liquid chromatography, and gas-solid chromatography. Gas-liquid chromatography is presently the most widely employed type and incorporates a nonvolatile liquid sorbent coated as a thin layer on an inner support structure, generally the inside surface of a capillary tube. The moving gas phase, called the carrier gas, flows through the chromatography column. The analyte partitions itself between the moving gas phase and the sorbent, and moves through the column at a rate dependent upon the partition coefficient or solubility of the analyte components. The analyte is introduced at the entrance end of the column within the moving carrier gas stream. The components making up the analyte become separated along the column and escape from the exit end of the column at intervals and in concentrations characteristic of the properties of the analyte components.

A detector, for example, a mass spectrometer, thermal conductivity detector or flame ionization detector (FID) at the exit end of the analytical column responds to the presence of analyte components. Upon combustion of the eluded material at an FID, charged species are formed in the flame. The flame behavior is monitored through a biased ion detector which, along with associated electronics, produces a chromatogram which is a time versus magnitude trace of the detector output. The trace for a complex analyte mixture includes numerous peaks of varying intensity. Since individual constituents of the analyte produce peaks at characteristic times and whose magnitude is a function of their concentration, much information is gained through an evaluation of the chromatogram.

Today there is an increased emphasis toward so-called "fast gas chromatography" or "fast GC". Applications include process stream monitoring, environmental monitoring, and IC engine exhaust gas analysis. Ideally, such a system would be capable of performing an analysis within several seconds, which using conventional approaches, would take several minutes or more. Increasing the speed of analysis can be achieved by providing a relatively short separation column, or by using other techniques for causing components of interest to traverse the column more quickly. In order to provide useful information, the individual analyte components must elute separately at the detector, thus producing distinct peaks. As the length of time over which the sample is injected at the inlet end of the separation column (injection time) increases, the peaks produced by elution of the components tend to broaden, smear, and overlap. It is, therefore, essential that a short duration sample "plug" be presented at the column inlet during injection in order to provide gas chromatography evaluation in a short period of time while providing acceptable resolution.

Various types of injection systems are presently known for placing a sample at the inlet end of a separation column. One approach uses a mechanical valve, which is controlled to intermittently communicate a sample stream with the analytical column as a sample plug. Previously known injection valves, however, have significant limitations in terms of their minimum injection time. Known mechanical valves also have shortcomings in terms of mechanical wear and contamination of the sample stream caused by the presence of lubricants and other impurities within the valve. In addition, valve elements can become coated with a sample which is retained and mixed with subsequent samples, and thus the system has an undesirable artifact termed a "memory" effect.

One facet of the present invention is to provide improved mechanical injection valves. The injection valves of this invention include a shuttle element which, in two described embodiments are moveable linearly, and in another embodiment moves rotationally. The shuttle has a small exit port through which a sample stream is discharged. The valves of this invention cause the shuttle exit port to be swept rapidly across an inlet of an analytical column as a means of creating a narrow sample plug. Carrier gases are routed through the device in a way that the sample stream is continually vented and the area of the column inlet is flushed with carrier gas between injections. It is believed that the injection valves in accordance with the present invention are capable of generating sample plugs as narrow as several milliseconds in duration. The injection valves of this invention may also be used for injecting a sample onto multiple columns in a programmed manner. Moreover, the valves may be used in the reverse sense for coupling multiple sources to a single outlet or column.

Another consideration which complicates efforts toward reducing analysis time is the result of the fundamental conflict between resolution of separated components and separation time. In general, as separation time increases, better separation of the individual constituents of an analyte mixture occurs, producing well defined distinct chromatograph peaks which do not overlap those of other components. In some instances, a mixture may contain components of interest having a relatively high boiling point which tend to elute well after initial peaks are produced. For such an analyte, if separation time is shortened and it is desired to evaluate the high boiling point components, the low boiling point components which elute faster tend to produce smeared and overlapped peaks with poor definition. In order to increase resolution of the low boiling point components, overall analysis time needs to be increased.

In accordance with the present invention, a high degree of resolution of output for specific mixture constituents is provided by using a multiple column system in which samples are injected into columns having differing separation characteristics. Such differing characteristics can be achieved through the use of columns having varying lengths, diameters, liquid or solid phase materials, carrier gas velocities, etc. Moreover, the speed of separation can be controlled by the temperature of the separation columns. Analyte eluted from the multiple columns is preferably evaluated at a single detector which produces a chromatogram which is a composite of outputs from the multiple columns. The characteristics of the columns and the injection sequence are preferably chosen so that significant peaks can be superimposed relative to the output of other columns in a single chromatogram which provides good resolution of all components of interest. The portions of a single column chromatogram which are ordinarily free of peaks can be used as an interval in which to insert peaks from another column related to specific compounds of interest. In this way a complex chromatogram including various constituents of an analyte can be created through an overlapping of the outputs of multiple columns. The system would, therefore, provide high resolution of relatively high boiling point components while providing fast overall analysis time and preserving resolution of relatively low boiling point components of a mixture. These advantages can be achieved through the use of a single detector which, in modern gas chromatography systems, may be a very costly component of the overall system.

Additional benefits and advantages of the present invention will become apparent to those skilled in the art to which this invention relates from the subsequent description of the preferred embodiments and the appended claims, taken in conjunction with the accompanying drawings.

BRIEF DESCRIPTION OF THE DRAWINGS

FIGS. 6a through 6c are chromatograms wherein

DETAILED DESCRIPTION OF THE INVENTION

Figure 1:
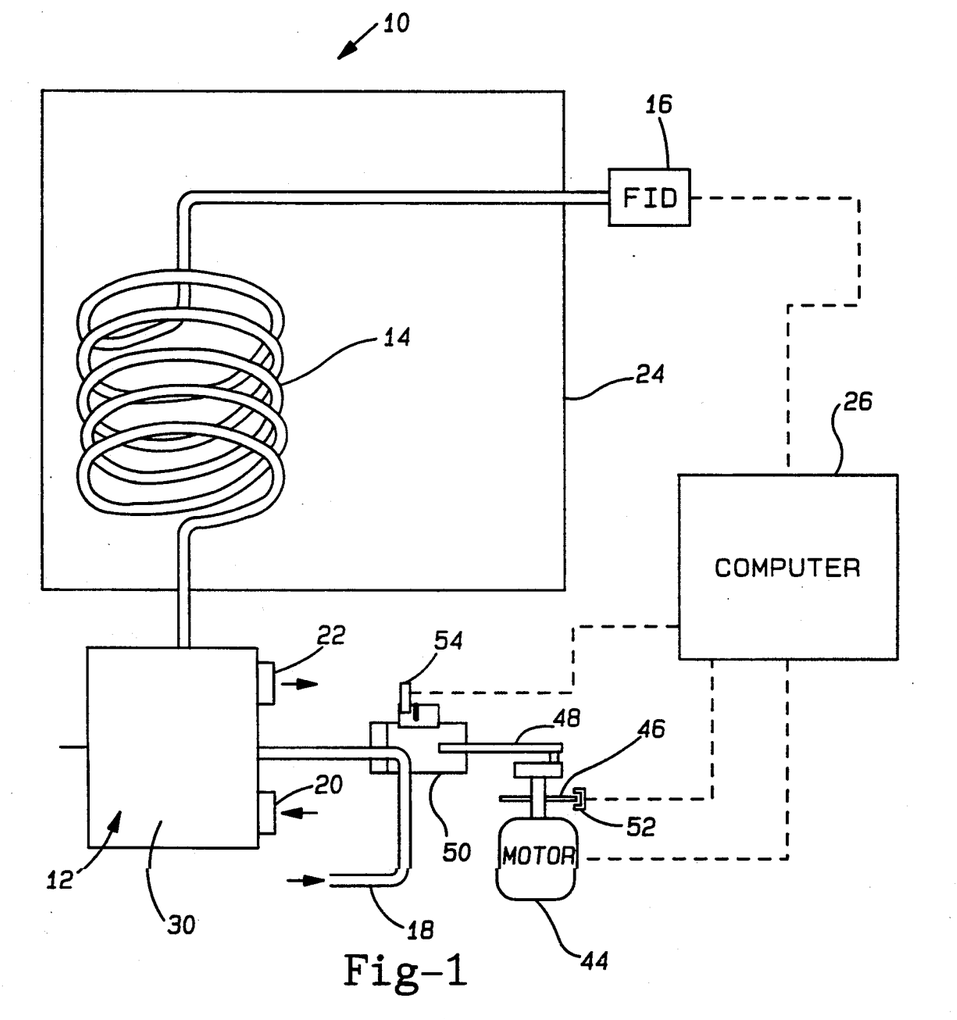
FIG. 1 is a schematic diagram of a gas chromatography system in accordance with the first embodiment of this invention incorporating a mechanical injection valve designed in accordance with this invention.

A gas chromatography (GC) system in accordance with a first embodiment of this invention is shown in diagrammatic fashion in FIG. 1 and is generally designated there by reference number 10. GC system 10 generally comprises an injection valve 12 for injecting a sample into separation column 14, the output of which is evaluated at detector 16. Injection valve 12 is shown in more detail in FIG. 2 and receives a sample vapor through capillary tube 18. The sample vapor flowing in tube 18 can be diluted and transported by a suitable transport gas which in some cases could be air. A supply of pure sample carrier gas which transports the sample through column 14 and also acts as a housing "flushing" gas is inputed at inlet 20 and exhausted at outlet 22. Samples are inputed into separation column 14 which may be of any conventional variety, such as fused silica glass and would typically be of the gas-liquid phase or gas-solid phase variety. Separation column 14 is shown enclosed within temperature control chamber 24 which allows the column temperature to be held precisely for providing the desired propagation rate of constituents of the analyte mixture. Materials which elute from column 14 are sensed by flame ionization detector (FID) 16. When components of the analyte pass through FID 16, charged species are formed which are detected by an electrometer (not shown). Computer 26 is provided both for system control and output data collection and reduction functions. As shown, the output from FID 16 is directed to computer 26 which, through an external plotter or monitor, generates a chromatogram.

Figure 2:
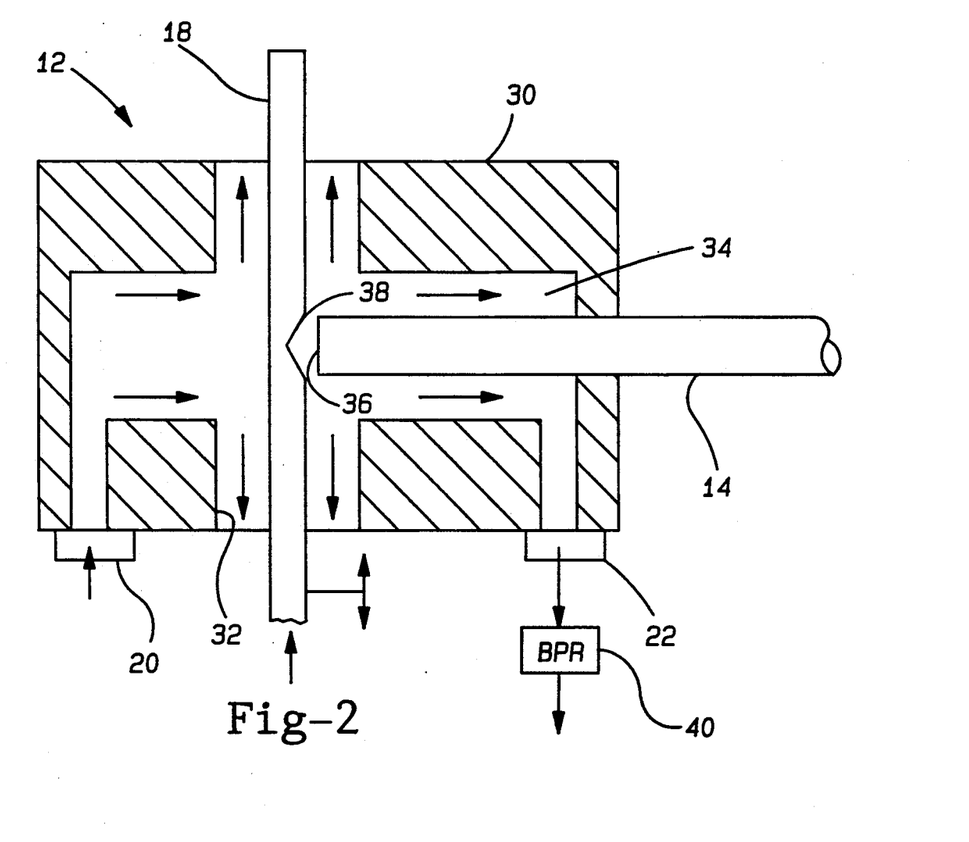
FIG. 2 is a cross sectional view of the mechanical injection valve shown in FIG. 1.

Now with reference to both FIGS. 1 and 2, the details of injection valve 12 and the mechanical system which actuates it are described. Injection valve 12 has a housing 30 which may be made, for example, from a machined metal block. Housing 30 includes a number of internal passages including bore 32 which receives capillary tube 18. Another cavity 34 accommodates analytical column 14 which has an entrance orifice 36 confronting capillary tube 18. Bore 32 closely receives capillary tube 18, although the clearances are greatly exaggerated in FIG. 2 for the sake of illustration. Carrier gas such as hydrogen or helium is inputed to the device through inlet 20. Since bore 32 provides clearance around capillary tube 18, the tube is suspended by gas flow as it escapes from housing 30, as shown by the gas flow arrows in FIG. 2. Capillary tube 18 features a small port 38 on one side. Capillary tube 18 acts as a "shuttle" element which is translated within housing 30, such that port 38 sweeps past column entrance orifice 36. A sample vapor continuously flows through capillary tube 18 and carrier gas continually flows into port 20. When port 38 is aligned with column 14, a small amount of sample is swept into the column.

During typical operation of injection valve 12, injection would be made as capillary tube port 38 is swept rapidly across column entrance orifice 36. Between injections, when capillary tube port 38 is not aligned with column entrance 36, the carrier gas sweeps the continuously flowing sample vapor away from the column entrance through intentional leaks along the tube bore 32 and further through the leaks provided past column 14. This flow is shown by the arrows in FIG. 2 and is generated as gas exits through carrier gas outlet 22. Preferably, a back pressure regulator 40, for example in the form of a short length of fused silica capillary tube is provided for regulation of the pressure of carrier gas within housing 30, thus controlling the flow rate of gases through the device. In order for valve 12 to operate properly, it is necessary that the inlet pressure of the sample vapor and the carrier gas be greater than that within column 14, and that of the environment surrounding housing 30.

Turning again to FIG. 1, a mechanism for translating capillary tube 18 will be described. A small motor 44 is provided with circular slotted disk 46 fastened to the output shaft which drives crankshaft 48. Crankshaft 48 is in turn attached to sliding block 50 which strokes in response to rotation of motor 44. Capillary tube 18 is coupled to sliding block 50 so that as the output shaft of motor 44 completes one revolution, capillary tube port 38 sweeps past column entrance 36 once in each direction. Two light interruption devices, each comprising a light source and photodetector, are used to control the injection valve 12 through computer 26. A first light interrupter 52 provides an output related to the presence of a pair of diametrically opposite slots within disk 46 and is used for positioning crankshaft 48. A second light interrupter 54 senses the position of sliding block 50 and interacts with a slotted tab positioned such that a tab slit is in a position to allow light to pass through it which signals an input to computer 26 at the moment that injection is occurring. Light interrupter 52 allows computer 26 to precisely control motor 44 to undertake one-half revolution and thus generate one sample injection. An output generated by light interrupter 54 signals computer 26 that an injection has been made, thus triggering data collection from FID 16.

While a motor type actuator has been described for translating capillary tube 18, numerous other devices could also be implemented. For example, electrical solenoids or fluid operated actuators could also be used. Moreover, injection of liquid samples may also be possible by prevaporizing the sample prior to introduction into valve 12. In addition, other types of carrier gas and detectors could also be employed.

Gas chromatography system 10 as described previously is believed capable of providing extremely small injection bandwidths, perhaps on the order of one to five milliseconds. This system would therefore be ideal for high speed gas chromatography. When used in conjunction with appropriate short lengths of separation column 14, some mixtures could be separated within only a few seconds. In providing rapid separation, GC system 10 could be applicable to process control and environmental monitoring applications. Injection valve 12 is also believed to be capable of providing low maintenance, repeated injections in that internal friction is minimized.

Figure 3:
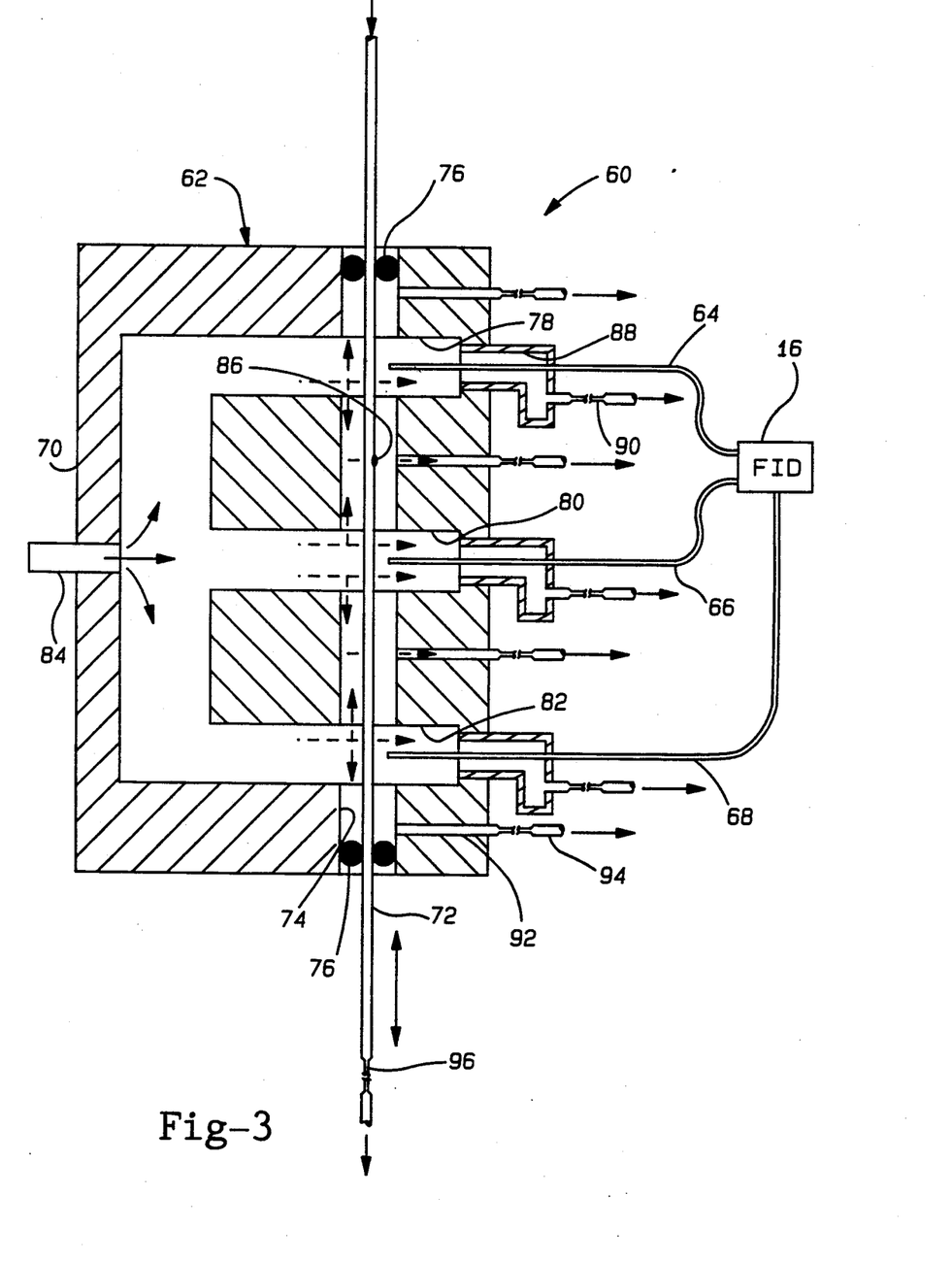
FIG. 3 illustrates a gas chromatography system in accordance with a second embodiment of this invention incorporating a mechanical injection valve for injecting a sample into three separate gas chromatography columns.

Now with reference to FIG. 3, a gas chromatography system according to a second embodiment is shown and is generally designated by reference number 60. GC system 60 incorporates an injection valve 62 having many of the features of injection valve 12 but provides multiple outlets to a series of three analytical separation columns 64, 66 and 68. Injection valve housing 70 includes a bore 74 for movement of capillary tube 72 as in the case of the prior embodiment. A pair of 0-rings 76 are disposed at opposite ends of bore 74 which aid in supporting the capillary tube and controlling gas flow leakage from housing 70. Three passageways 78, 80 and 82 are provided to accommodate separation columns 64, 66 and 68, respectively. As in the prior embodiment, a clearance is provided for carrier gas inputed at inlet 84 to sweep across the entrance orifices of the columns. Capillary tube 72 is constructed like that of the prior embodiment in that it has a small port 86 through which the sample vapor (which may be entrained in a flow of a suitable transport gas) continuously flows, and provides a means for introducing the sample to one of the columns when it is swept past the inlet orifice of a column.

A translation system, which could be similar to that shown in conjunction with the first embodiment could be provided for injection valve 62. Alternatively, solenoids, fluid devices, or other linear actuators could be used.

Injection valve 62 includes a number of passageways for the control of carrier gas flow. As shown, outlet ports 88 are provided having flow restrictors 90 which create a small leak so that carrier gas will flow along the separation columns as shown by the arrows in FIG. 3. This assures that the column entrance orifices are swept by clean carrier gas between injections and also directs the sample vapor flow into the column orifices when the port 86 is aligned with them. When capillary tube port 86 is placed at a "park" position between columns 64 and 66 as shown in FIG. 3, (or above column 64 or below columns 66 or 68) it is necessary to assure that the continuously flowing sample vapor will not inadvertently flow into one of the separation columns. Therefore, passageways 92 are provided with flow restrictors 94 which provide additional flow paths for carrier gas for sweeping the sample out of housing 70 where it is vented to atmosphere or into a trapping chamber. Still another restrictor 96 is provided at one end of capillary tube 72 and enables the sample vapor pressure within the tube to be adjusted to a level above that within housing 70. As in the prior embodiment, proper operation of injection valve 62 requires that the pressure of both the carrier gas supply and sample vapor be greater than that within the separation columns 64, 66 and 68, and the environment surrounding housing 70.

To deliver a sample plug to one of columns 64, 66 or 68, capillary tube 72 is vertically translated as shown by the solid arrows in FIG. 3. As port 86 sweeps past the inlet of one of the columns, a sample is delivered to that column. By adjusted the speed of translation, in relation to the relative sizes of the column inlet orifices and tube port 86, the injection time width of the sample plug can be adjusted. Between injections, port 86 is parked away from the columns, as shown in FIG. 3.

Figure 4:
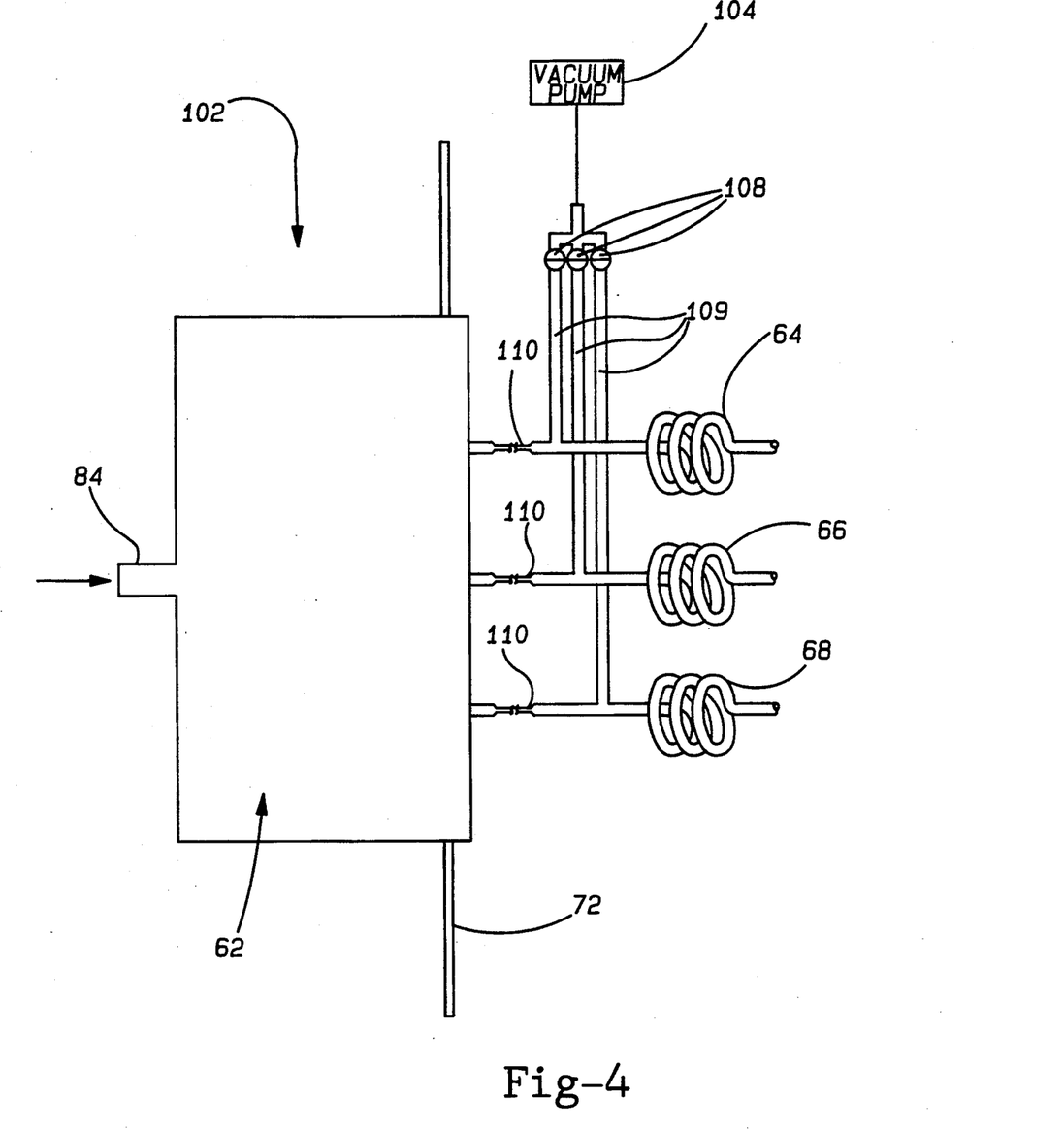
FIG. 4 is a gas chromatography system in accordance with a third embodiment of this invention which is identical to that shown in FIG. 3 with the addition of a vacuum pump for column backflushing.

FIG. 4 shows a modification of the system shown in FIG. 3 which is identified as GC system 102. System 102 is identical to that shown in FIG. 3 except that a rapid column backflushing capability is incorporated. Vacuum pump 104 is connected via vent lines 109 to each of separation columns 64, 66 and 68 through valve 108. When it is desired to backflush a column to remove a prior sample mixture and particularly any high boiling point components which have not eluted, a valve 108 for that column is opened, communicating vacuum pump 104 to the column. In order to assure a backwards fluid flow through the columns, flow restrictors 110 are provided. In all other respects, GC system 102 operates like that of the embodiment shown in FIG. 3.

Figure 5:
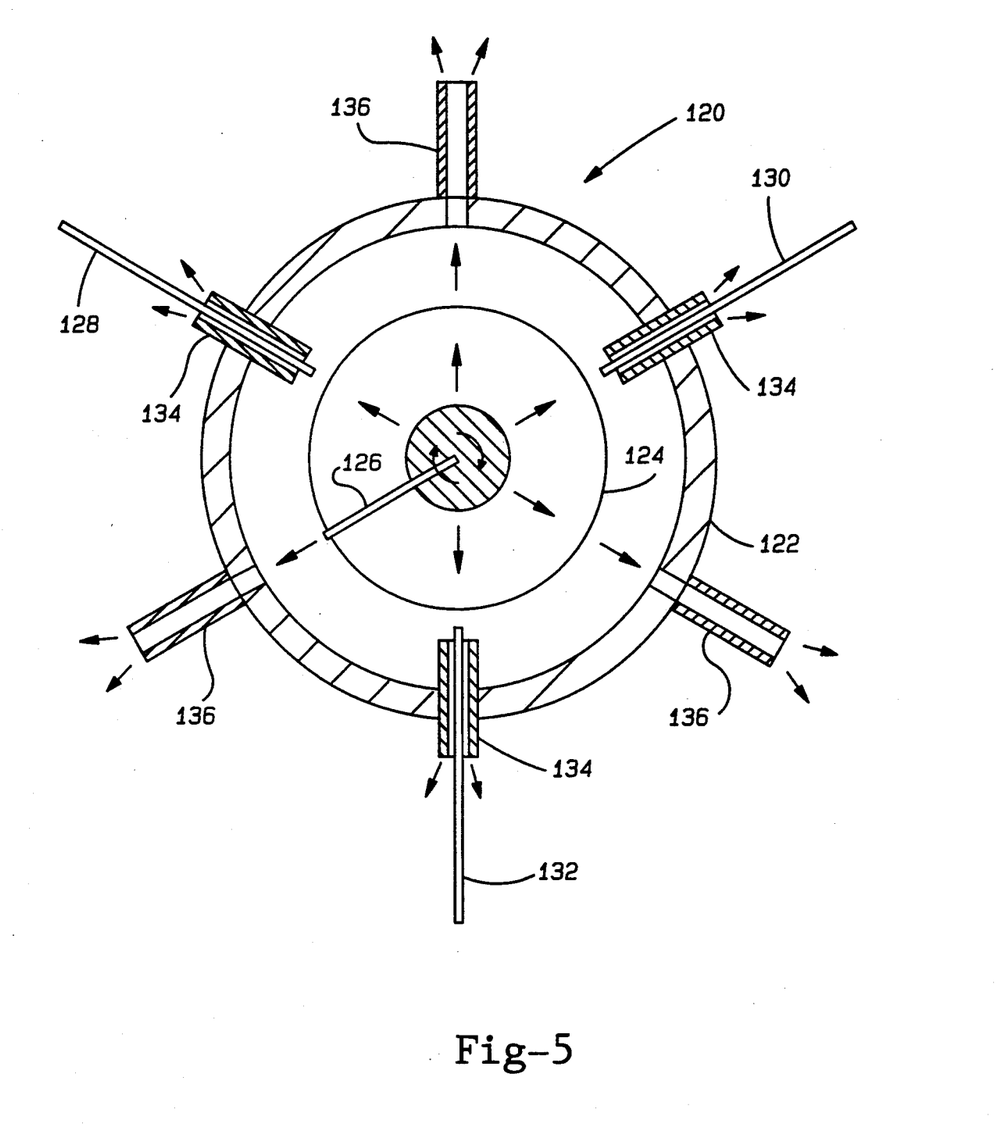
FIG. 5 shows an injection valve for a gas chromatography system in accordance with a fourth embodiment of this invention incorporating a rotary shuttle for enabling a single source to be inputed into multiple gas chromatography columns.

Now with reference to FIG. 5, an injection valve in accordance with a fourth embodiment of this invention is shown and is generally designated by reference number 120. Injection valve 120 bears a resemblance to injection valve 62 in that it provides multiple outlets for a single inlet. Valve 120 differs, however, in that the "shuttle" element is actuated through rotational motion. As shown, injection valve 120 has a cylindrical housing 122 having a central rotary plug 124. A delivery tube 126 rotates with plug 124 and conducts a continuous flow of a sample vapor. A carrier gas flow is inputed into housing 122 at near the axis of rotation of plug 124. Located around the periphery of housing 122 are three separation columns 128, 130 and 132. The separation columns are surrounded by enlarged diameter tubes 134 which provide an intentional carrier gas leak along the separation columns. As mentioned with the prior embodiments, this gas flow is intended to provide for aiding in injection and clearing the column entrances between injections. Vent passages 136 are provided at peripheral positions intermediate the columns and allow the carrier gas to escape the device when delivery tube 126 is positioned at a park position as shown in FIG. 5 between the separation columns. This gas flow removes excess sample gas and any contaminants in the system. As in the case of the prior embodiments, the pressure of the carrier gas and sample vapor sources is higher than that of a lower pressure receiver device located at the end of separation column 128, 130 and 132 and the environment surrounding housing 122. For example, in a gas chromatography application, the receiver would likely be an atmospheric or pressure detector such as an FID or a sub-ambient pressure type such as a mass spectrometer.

To deliver sample gas to one of the separation columns, delivery tube 126 is rotated as shown by the curved arrows from the position shown in the Figure. When the end of sample delivery tube 126 is aligned with an end of one of the separation columns, sample gas vapor will pass into that column. By use of a precise rotational control such as that obtained with a stepper motor, alignment position of a few micrometers can be achieved. The length of the sample gas injection can be controlled by a computer as in the prior embodiments.

As in the prior embodiments, the rate of delivery of the sample vapor gas through delivery tube 126 is controlled by the sample vapor gas delivery pressure, the pressure within housing 122, and the pneumatic restriction imposed by delivery tube 126. The rate of gas flow through the separation columns depends on the pressure within housing 122, the pressure at the downstream end of the column and the pneumatic restriction imposed by the column.

In addition to gas chromatography applications in which a vapor source communicates with multiple separation columns, additional applications are possible for the injection valves of this invention. For example, valves 12, 62 and 120 could be used to regulate the introduction of gases into chambers as in microchip processing applications where precise quantities of chemically clean and pure gases are necessary. In another application, if the separation columns 64, 66 and 68 of valve 62, or columns 128, 130 and 132 of valve 120 are replaced by tubes communicating with higher pressure gas sources and delivery tube 72 or 126 is instead a receiver tube, the devices can be operated as a source multiplexing device which can select any one of several source vapor gas supplies for transmission to the receiver which could be a separation column. In addition, the devices could be used to connect several gas chromatography columns to a single detector for column multiplexing.

For the embodiments shown in FIGS. 3, 4 and 5, the multiple separation columns could have different separation characteristics such as by being operated at different temperatures. The systems are capable of delivering samples to the multiple columns with an adjustable and programmable time interval between injections on the respective columns. The outputs of the multiple columns can be combined or multiplexed to form a single chromatogram from FID 16. In this way, the chromatographic time dimension can be used more efficiently.

Figure 6A:
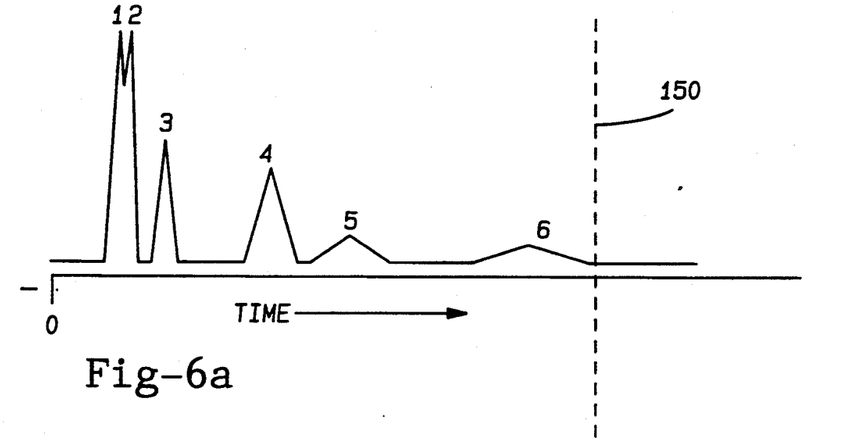
FIG. 6a shows a representative chromatogram taken from a first column.

This mode of operation is best explained with reference to FIGS. 6a, 6b and 6c. FIG. 6a represents a chromatogram which provides rapid separation for most of the representative analyte components, with component peaks designated by reference numbers 1 through 6 and injection occurring at time zero. As shown in FIG. 6a, a pair of low boiling point components identified as peaks 1 and 2 are not well separated. While these components can be separated at a lower column temperature (or by other approaches of increasing overall separation time), the last components 5 and 6 would then elute much later, thus significantly increasing the total separation time. The chromatogram of FIG. 6b shows the first two components identified by peaks 1 and 2 well separated on a second column which has a different selectivity than the first column, or the same selectivity but operated at a lower temperature.

Figure 6B:
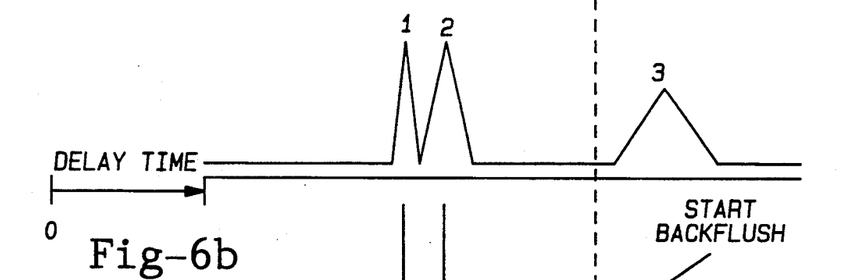
FIG. 6b shows a chromatogram taken from a second column in a multi-column system according to this invention.
Figure 6C:
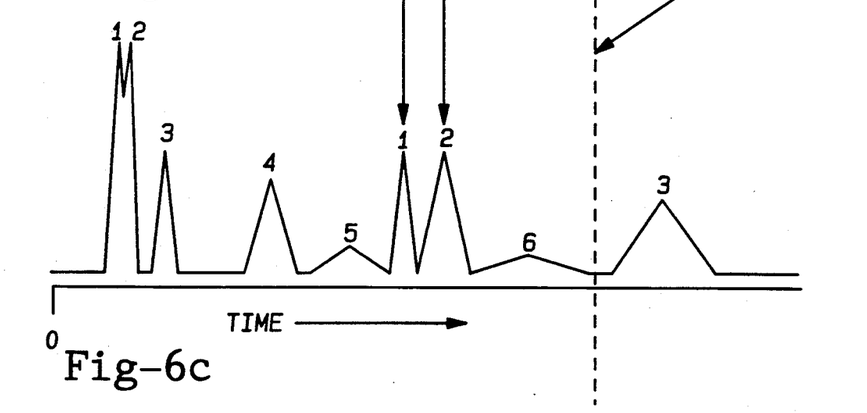
FIG. 6c shows the peaks of the chromatograms of FIGS. 6a and 6b superimposed.

If the sample injection on the second column is delayed as shown in FIG. 6b and the outputs of both columns combined before the detector, components 1 and 2 from the second column can be inserted into the gap present between component peaks 5 and 6 in the chromatogram of FIG. 6a. This combination is represented by the chromatogram of FIG. 6c. The vertical dotted line 150 in FIGS. 6a through 6c represents the start of backflush operation. As shown in FIG. 6b, the peak 3 and those occurring thereafter would be backflushed. This would be appropriate since peak 3 is well separated in the chromatogram of 6a and thus would not be of interest in the chromatogram of FIG. 6b. The appropriate injection sequence with time delays is achieved by the use of computer 26 and appropriate translation system.

While the above example involves the use of two separation columns, the same principles would apply to the use of a three column system, with the outputs of the columns appropriately phased to efficiently use the time domain.

In another system for column multiplexing, columns 64, 66 and 68, or columns 128, 130 and 132 could have identical separation characteristics, with injection occurring sequentially. In this manner, the substantial idle time for the detector 16 and data reduction system 26 present in a single column system could be utilized. The time delay between injections would preferably be set such that a non-overlapping series of chromatograms is generated. With reference to the figures, such chromatograms can be visualized as a series of chromatograms as shown in FIG. 6a with the start time of the next trace at the start of backflush time designated by reference number 150. Such a system would provide superior process control or monitoring performance, especially where transient sample compositions are encountered.

While the above description constitutes the preferred embodiments of the present invention, it will be appreciated that the invention is susceptible of modification, variation and change without departing from the proper scope and fair meaning of the accompanying claims.

We claim:

1. A gas chromatography injection valve for controlling the flow of a sample vapor to an analytical separation column, comprising:
   a housing having an internal passageway and an outlet port communicating with said separation column,
   a linearly moveable shuttle within said housing having an injection port communicating with said sample vapor,
   actuator means for moving said shuttle within said housing to cause said injection port to be moveable between an injection position with said injection port in registry with said outlet port providing fluid communication between said ports, to a non-injection position with said injection port and said outlet port out of registry,
   inlet means for communicating said housing internal passageway with a source of a flushing gas, and
   means for controlling the flow of said flushing gas through said housing such that said sample vapor flowing into said housing does not communicate between said injection port and said outlet port when said shuttle is in said non-injection position said means for controlling including at least one capillary flow restrictor allowing said flushing gas to be continuously vented from said housing and at least one sealing element acting as a bearing for allowing said linear movement of said shuttle while controlling leakage of said flushing gas.

2. A gas chromatography injection valve according to claim 1 wherein said housing defines two or more of said outlet ports with each of said outlet ports communicating with separate analytical separation columns.

3. A gas chromatography injection valve according to claim 2 wherein in said non-injection position said injection port is positioned between adjacent of said outlet ports.

4. A gas chromatography injection valve according to claim 1 wherein said shuttle comprises an injection tube linearly translatable within said housing and extending exteriorly of said housing, and wherein said injection port comprises an aperture along said injection tube.

5. A gas chromatography injection valve according to claim 4 wherein said outlet port is formed by an outlet tube oriented perpendicular to said injection tube with said outlet port opening at the end of said outlet tube adjacent said injection tube.

6. A gas chromatography injection valve according to claim 5 wherein said means for controlling the flow of said flushing gas comprises gas flow passages causing said flushing gas to flow along said outlet tube and out of said housing, and along said injection tube and out of said housing.

7. A gas chromatography injection valve according to claim 5 wherein said means for controlling the flow of said flushing gas comprises gas flow passages causing said flushing gas to flow along said outlet tube.

8. A gas chromatography injection valve according to claim 1 wherein said means for controlling the flow of said flushing gas further includes a vent port positioned adjacent said injection port when said shuttle is in said non-injection position and wherein said capillary flow restrictor communicates with said vent port to permit control of the flow of said flushing gas through said vent port.

9. A gas chromatography injection valve according to claim 1 further comprising an actuator external of said housing for causing displacement of said shuttle and at least one sealing element for controlling leakage of said flushing gas from between said housing and shuttle.

10. A gas chromatography injection valve for controlling the flow of a sample vapor to an outlet comprising:
    a housing having an internal passageway and at least two outlet ports with at least one of said outlet ports for connection to an analytical separation column,
    a shuttle tube linearly displaceable within said housing and having an injection port communicating with said sample vapor,
    actuator means for moving said shuttle within said housing to cause said injection port to be moveable between an injection position with said injection port in registry with one of said outlet ports providing fluid communication therebetween, to a non-injection position with said injection port out of registry with each of said outlet ports,
    inlet means for communicating said housing passageway with a source of a flushing gas, and
    means for controlling the flow of said flushing gas through said housing such that said sample vapor flowing into said housing does not communicate between said injection port and any of said outlet ports when said shuttle is in said non-injection position.

11. A gas chromatography injection valve according to claim 10 wherein each of said outlet ports is formed by an outlet tube oriented normal to said shuttle tube with one of said outlet ports opening at the end of said outlet tube adjacent said shuttle tube.

12. A gas chromatography injection valve according to claim 11 wherein said means for controlling the flow of said flushing gas comprises gas flow passages causing said flushing gas to flow along said outlet tube and out of said housing, and along said shuttle tube and out of said housing.

13. A gas chromatography injection valve according to claim 11 wherein said outlet tubes are separated and generally parallel to one another and in said non-injection position said injection port is positioned between adjacent of said outlet ports.

14. A gas chromatography injection valve according to claim 10 wherein each of said outlet ports communicating with separate analytical separation columns.

15. A gas chromatography injection valve according to claim 14, wherein said means for controlling the flow of said flushing gas includes a vent port positioned adjacent said injection port when said shuttle is in said non-injection position.

16. A gas chromatography injection valve for controlling the flow of a supplied fluid to an outlet, comprising:
    a housing having an internal passageway and a first port,
    a plug rotationally displaceable within said housing and having a second port,
    actuator means for rotating said plug within said housing to cause said second port to be moveable between an injection position with said first and second ports in registry providing fluid communication between said ports, to a non-injection position with said ports out of registry, inlet means for communicating said housing internal passageway with a source of a flushing gas, and means for controlling the flow of said flushing gas through said housing such that said supplied fluid flowing into said housing does not communicate between said first and second ports when said plug is in said non-injection position.

17. A gas chromatography injection valve according to claim 16 wherein said supplied fluid is a sample vapor and said second port communicates with said sample vapor and said first port communicates with an analytical separation column.

18. A gas chromatography injection valve according to claim 17 wherein said first port is formed by an outlet tube oriented with an end of said outlet tube adjacent said second port when said plug is in said injection position.

19. A gas chromatography injection valve according to claim 18 wherein said means for controlling the flow of said flushing gas comprises gas flow passages causing said flushing gas to flow along said outlet tube.

20. A gas chromatography injection valve according to claim 18 wherein said housing defines more than one of said first ports with each of said first ports defining distinct flow paths within said housing.

21. A gas chromatography injection valve according to claim 20 wherein in said non-injection position said plug is located with said second port positioned between adjacent of second ports.

22. A gas chromatography injection valve according to claim 20 wherein said means for controlling the flow of said flushing gas includes a vent port positioned adjacent said second port when said plug is in said non-injection position.

23. A gas chromatography system for the analysis of an analyte comprising:

at least two analytical separation columns, said columns exhibiting differing separation characteristics, detector means for sensing the presence of components of said analyte eluting from said columns, and injection means for injecting an unseparated sample of said analyte into said columns whereby said separation characteristics of said columns are selected and said unseparated sample is sequentially injected into said columns such that said components eluting from each of said columns is intended to emphasize certain components of said analyte and wherein said components are sensed by said detector means at distinct time intervals.

24. A gas chromatography system according to claim 23 wherein said detector means comprises a single detector receiving components of said analyte eluting from each of said columns.

25. A gas chromatography system according to claim 23 wherein said separation characteristics of said columns and said injection sequence are selected such that said certain components of said analyte eluting from one of said columns eludes during a time when the output of another of said columns is negligible.

26. A gas chromatography system according to claim 23 further comprising means for backflushing said columns.

27. A gas chromatography system according to claim 23 wherein said injection means comprises a mechanical injection valve having a housing having an internal passageway and at least two outlet ports communicating with said analytical columns and a moveable shuttle element having an injection port with said shuttle moveable from an injection position wherein said injection port and one of said outlet ports are aligned causing injection, to a non-injection position with said injection port out of registry with each of said outlet ports.

28. A gas chromatography system according to claim 23 wherein said injection means causes an injection into one of said columns to occur after a predetermined time delay after injection into another of said columns.

29. A gas chromatography system for the analysis of an analyte comprising:

at least two analytical separation columns, said columns exhibiting differing separation characteristics, a detector receiving analyte components eluted from each of said columns for sensing the presence of analyte components being eluted, a mechanical injection valve for injecting an unseparated sample of said analyte into said columns said injection valve having a housing with an internal passageway and at least two outlet ports communicating with said analytical columns and a moveable shuttle element having an injection port from which said unseparated sample flows and said shuttle element moveable from an injection position wherein said injection port is aligned with one of said outlet ports to a non-injection position in which said injection port is out of registry with each of said outlet ports, and controller means for operating said injection valve such that said analyte is sequentially injected into said columns in a timed sequence such that the components of interest are eluted from said columns and sensed by said detector at distinct time intervals.

30. A gas chromatography injection valve for controlling the flow of a continuously supplied sample vapor to at least one outlet comprising:

a housing having an internal chamber and at least one outlet port for connection to an analytical separation column, said chamber further defining an elongated bore, a shuttle tube linearly displaceable within said housing bore and having a hollow inside passageway and a vapor injection port in the form of an aperture through a wall of said tube, actuator means for moving said shuttle tube within said housing bore to cause said injection port to be moveable between an injection position with said injection port and said outlet port in registry providing fluid communication between said ports, and to first and second non-injection positions with said ports out of registry and said non-injection positions corresponding to said injection port on opposite sides of said outlet port along said bore, inlet means for communicating said housing chamber with a source of a flushing gas, and first and second vent passageways within said housing for permitting leakage of said flushing gas from said housing, said vent passageways positioned adjacent said injection port when said shuttle tube is in said non-injection positions, capillary flow restrictors connected to said outlet ports for controlling the flow of said flushing gas from said vent passageways, and at least one sealing element within said bore providing a bearing for said shuttle tube and controlling leakage of said flushing gas along said tube.

31. A gas chromatography injection valve according to claim 30 wherein said outlet port is formed by an outlet tube oriented normal to said shuttle tube with said housing port opening at the end of said outlet tube adjacent said shuttle tube.

* * * * *